United States Patent
Lorenzo et al.

(10) Patent No.: US 11,872,119 B2
(45) Date of Patent: Jan. 16, 2024

(54) COMPOSITE VASCULAR FLOW DIVERTER

(71) Applicant: DePuy Synthes Products, Inc., Raynham, MA (US)

(72) Inventors: Juan Lorenzo, Davie, FL (US); Robert Slazas, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 301 days.

(21) Appl. No.: 17/119,256

(22) Filed: Dec. 11, 2020

(65) Prior Publication Data

US 2021/0093442 A1    Apr. 1, 2021

Related U.S. Application Data

(62) Division of application No. 15/416,324, filed on Jan. 26, 2017, now Pat. No. 10,881,497.

(51) Int. Cl.
    *A61F 2/07*    (2013.01)
    *A61F 2/82*    (2013.01)
    (Continued)

(52) U.S. Cl.
    CPC .............. *A61F 2/07* (2013.01); *A61F 2/82* (2013.01); *A61F 2002/061* (2013.01);
    (Continued)

(58) Field of Classification Search
    CPC ........ A61F 2/07; A61F 2/82; A61F 2002/061; A61F 2002/072; A61F 2002/823;
    (Continued)

(56) References Cited

U.S. PATENT DOCUMENTS

| | | | | |
|---|---|---|---|---|
| 4,719,924 A | * | 1/1988 | Crittenden | ...... A61M 25/09033 604/528 |
| 5,396,902 A | | 3/1995 | Brennen et al. | |

(Continued)

FOREIGN PATENT DOCUMENTS

| | | |
|---|---|---|
| CN | 103071195 A | 5/2013 |
| CN | 105726163 A | 7/2016 |

(Continued)

OTHER PUBLICATIONS

Notification of Reasons for Refusal issued in Japanese Patent Application No. 2018-011325 dated Oct. 5, 2021, English translation.

(Continued)

*Primary Examiner* — Darwin P Erezo
*Assistant Examiner* — Brigid K Byrd
(74) *Attorney, Agent, or Firm* — Troutman Pepper Hamilton Sanders LLP

(57) ABSTRACT

A vascular flow diverter includes a tubular mesh framework which includes a mesh cover and an opening. The tubular mesh framework is collapsible and configured to expand from a collapsed shape to a tubular shape when the vascular flow diverter is deployed. The mesh cover conforms to the shape of the tubular mesh, is surrounded by the tubular mesh framework, and is less porous than the tubular mesh framework. The opening is located within the mesh cover. A delivery wire passes through the opening in order to guide the flow diverter into place over an aneurysm.

18 Claims, 5 Drawing Sheets

(51) Int. Cl.
*A61F 2/966* (2013.01)
*A61F 2/06* (2013.01)

(52) U.S. Cl.
CPC ... *A61F 2002/068* (2013.01); *A61F 2002/072* (2013.01); *A61F 2002/823* (2013.01); *A61F 2220/005* (2013.01); *A61F 2220/0058* (2013.01); *A61F 2250/0023* (2013.01); *A61F 2250/0039* (2013.01); *A61F 2250/0098* (2013.01)

(58) Field of Classification Search
CPC ........ A61F 2220/005; A61F 2220/0058; A61F 2250/0039; A61F 2250/0098; A61F 2/95–97; A61B 2017/1205–2017/12095; A61M 2025/0079; A61M 2025/0042; A61M 25/0147
See application file for complete search history.

(56) References Cited

U.S. PATENT DOCUMENTS

| | | | |
|---|---|---|---|
| 5,911,725 A | 6/1999 | Boury | |
| 5,951,599 A * | 9/1999 | McCrory | A61F 2/07 623/1.1 |
| 5,980,554 A | 11/1999 | Lenker et al. | |
| 6,093,199 A * | 7/2000 | Brown | A61B 17/12118 606/200 |
| 6,183,495 B1 | 2/2001 | Lenker et al. | |
| 6,391,037 B1 | 5/2002 | Greenhalgh | |
| 6,409,683 B1 | 6/2002 | Fonseca et al. | |
| 6,613,074 B1 | 9/2003 | Mitelberg et al. | |
| 7,156,871 B2 | 1/2007 | Jones et al. | |
| 8,182,544 B2 | 5/2012 | Cheng et al. | |
| 8,968,390 B2 * | 3/2015 | Richter | A61F 2/07 606/198 |
| 9,232,992 B2 | 1/2016 | Heidner | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 2003/0135259 A1 | 7/2003 | Simso | |
| 2003/0139802 A1 * | 7/2003 | Wulfman | A61B 17/12022 623/1.15 |
| 2005/0137680 A1 * | 6/2005 | Ortiz | A61F 2/90 623/1.53 |
| 2005/0197687 A1 * | 9/2005 | Molaei | A61L 31/088 623/1.2 |
| 2006/0064151 A1 | 3/2006 | Guterman | |
| 2008/0281350 A1 | 11/2008 | Sepetka | |
| 2009/0318948 A1 | 12/2009 | Linder et al. | |
| 2010/0131002 A1 | 5/2010 | Connor et al. | |
| 2010/0324649 A1 | 12/2010 | Mattsson | |
| 2011/0022149 A1 | 1/2011 | Cox et al. | |
| 2011/0160833 A1 * | 6/2011 | Gonzalez | A61F 2/856 623/1.11 |
| 2012/0191171 A1 | 7/2012 | Milijasevic et al. | |
| 2012/0226343 A1 | 9/2012 | Vo et al. | |
| 2012/0283768 A1 | 11/2012 | Cox et al. | |
| 2013/0131712 A1 | 5/2013 | Hines | |
| 2013/0231732 A1 | 9/2013 | Vonderwalde et al. | |
| 2014/0135812 A1 | 5/2014 | Divino et al. | |
| 2014/0200607 A1 | 7/2014 | Sepetka et al. | |
| 2014/0249620 A1 | 9/2014 | Carman et al. | |
| 2015/0066127 A1 * | 3/2015 | Johnson | A61F 2/90 623/1.11 |
| 2015/0081003 A1 | 3/2015 | Wainwright et al. | |
| 2015/0142043 A1 | 5/2015 | Furey | |
| 2015/0216684 A1 * | 8/2015 | Enzmann | A61F 2/848 623/1.36 |
| 2016/0262880 A1 | 9/2016 | Li et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0065401 A1 * | 3/2017 | Fearnot | A61F 2/07 |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |

(56) References Cited

U.S. PATENT DOCUMENTS

| | | |
|---|---|---|
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

FOREIGN PATENT DOCUMENTS

| | | | |
|---|---|---|---|
| CN | 106232059 A | 12/2016 | |
| JP | 2001-509412 A | 7/2001 | |
| JP | 2008-536586 A | 9/2008 | |
| JP | 2012-187325 A | 10/2012 | |
| JP | 2016-533833 A | 11/2016 | |
| WO | 2009/019664 A2 | 2/2009 | |
| WO | WO-2009019664 A2 * | 2/2009 | ....... A61B 17/12022 |
| WO | 2009/103125 A1 | 8/2009 | |
| WO | 2015/179377 A1 | 11/2015 | |

OTHER PUBLICATIONS

Notification of Reasons for Refusal issued in Japanese Patent Application No. 2018-011325 dated May 17, 2022, English translation.

Notification of Reasons for Refusal issued in Japanese Patent Application No. 2021-210495 dated Feb. 14, 2023, English translation only.

Struffert, T., et al. "Intravenous flat detector CT angiography for non-invasive visualization of intracranial flow diverter: technical feasibility" Eur Radiol 21:1797-1801 (2011) cited in CN SR submitted herewith.

Chinese Office Action and Search Report issued in Chinese Patent Application No. 201810076895, Office Action dated Apr. 2, 2021, Search Report dated Mar. 24, 2021, with machine translation.

\* cited by examiner

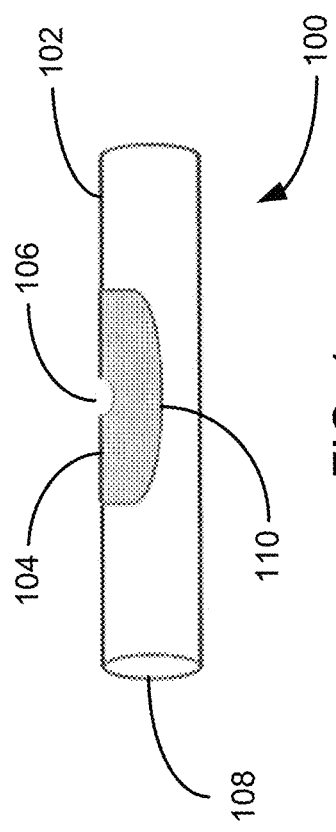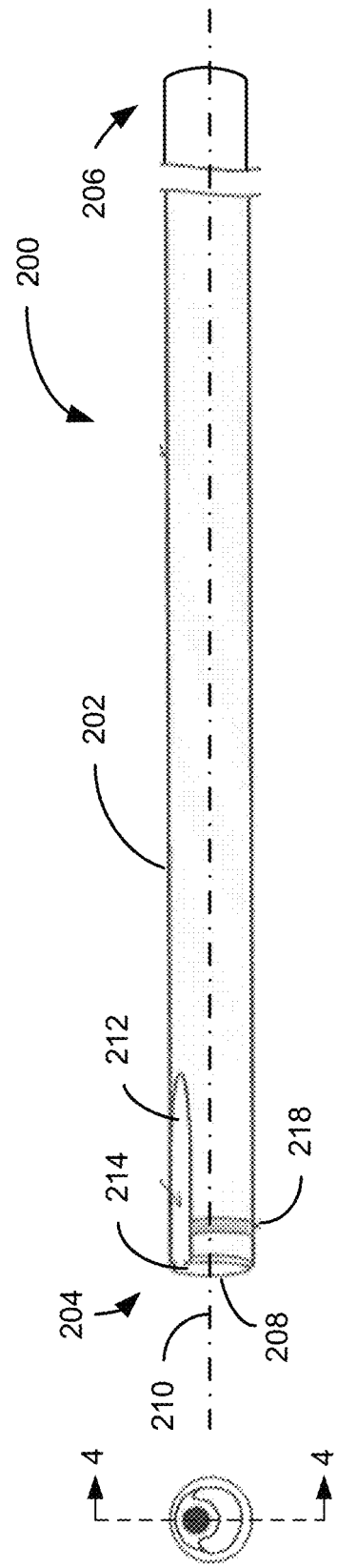
FIG. 1
FIG. 2

COMPOSITE VASCULAR FLOW DIVERTER

CROSS-REFERENCE TO RELATED APPLICATIONS

This application claims priority to U.S. patent application Ser. No. 15/416,324, filed on Jan. 26, 2017, the disclosure of which is herein incorporated by reference in its entirety.

FIELD OF INVENTION

The disclosure relates generally to intravascular medical devices. The disclosure relates more specifically to medical devices for treating vascular trauma and deformities.

BACKGROUND

Current vascular flow diverters consist of low-porosity braids that are deployed across the neck of the aneurysm and cover not only the periphery of the vessel across the neck of the aneurysm, but also a segment of otherwise healthy vessel proximal and distal to the neck of the aneurysm. Thromboembolic complications commonly result from these types of devices. Patients with such devices are prescribed long-term medication to alleviate the risk for device thrombosis.

The ideal intra-luminal flow diverter would treat the neck of the aneurysm only, thus minimizing the amount of metal in the lumen of the vessel and the potential for thromboembolic complications. However, positioning of a neck cover against the neck of the aneurysm in a three-dimensional space under fluoroscopy guidance is difficult with currently available imaging technologies.

No intra-vascular devices are commercially available that minimize the amount of metal in the vessel by targeting only the neck of the aneurysm. There are commercially available devices that attempt to treat the neck of the aneurysm intra-saccular, such as various aneurysm emobolization systems (e.g. embolic coils).

SUMMARY

The present disclosure describes various examples of an intra-vascular flow-diverting device designed to minimize the amount of metal in the vessel by targeting only the neck of an aneurysm, devices for deploying the intra-vascular flow-diverting device, and methods for guiding and deploying a flow diverting device to cover the neck of an aneurysm.

In one example of the disclosure, a vascular flow diverter includes a tubular mesh framework which includes a mesh cover and an opening. The tubular mesh framework is collapsible and configured to expand from a collapsed shape to a tubular shape when the vascular flow diverter is deployed. The mesh cover conforms to the shape of the tubular mesh, is surrounded by the tubular mesh framework, and is less porous than the tubular mesh framework. The opening is located within the mesh cover.

In one example, the tubular mesh framework has a circular cross section. In one example, the mesh cover has a rounded perimeter. In another example, the mesh cover has a circular perimeter. In some examples, the mesh cover is integrated with the tubular mesh framework. In other examples, the mesh cover is separate from and attached to the tubular mesh framework. In one example, the mesh cover is attached to the tubular mesh framework by welding. In another example, the mesh cover is attached to the tubular mesh framework by interlacing mesh strands of the mesh cover with mesh strands of the tubular mesh framework.

In one example of the disclosure, a device for deploying a vascular flow diverter includes a hollow microcatheter which includes a tubular outer wall, a distal end, and a proximal end. In one example, the distal end of the microcatheter includes a transverse opening which is substantially perpendicular to a longitudinal axis of the microcatheter and also includes a longitudinal opening which is substantially parallel to the longitudinal axis. The longitudinal opening intersects the transverse opening. The device also includes a delivery wire which includes a distal section, a proximal section, and a junction between the distal section and the proximal section. At least a portion of the distal section of the delivery wire is configured to adopt a curved configuration. The distal section has a smaller cross section than the proximal section.

In one example, the portion of the distal section of the delivery wire configured to adopt a curved configuration is pre-formed into the curved configuration and configured to revert to the curved configuration from a straightened configuration when the distal section of the delivery wire is deployed from the microcatheter In another example, the delivery wire includes a pull wire. The pull wire is positioned in a lumen of the delivery wire and terminates at a tip of the distal section. A proximal end of the pull wire may be pulled to apply tension to the pull wire, which draws at least a portion of the distal section of the delivery wire into a curved configuration.

In one example, a radiopaque marker may be fixed to the junction between the distal section and the proximal section of the delivery wire. In another example, a radiopaque marker may be fixed to the tip of the distal section of the delivery wire. In another example, the distal tip of the distal section of the delivery wire may be a coil formed from radiopaque material. In another example, a radiopaque marker may be fixed to the distal end of the microcatheter. In one example, the radiopaque marker fixed to the distal end of the microcatheter may be located between the transverse opening and a proximal end of the longitudinal opening. In a further example, the radiopaque marker fixed to the distal end of the microcatheter includes a split ring shape. In another further example, the split of the split ring shape is located astride the longitudinal opening of the microcatheter.

In one example of the disclosure, a method for deploying the vascular flow diverter includes advancing a microcatheter in a distal direction across a neck of an aneurysm in a blood vessel, advancing a distal tip of a delivery wire out of the microcatheter, rotating the microcatheter so that the curved delivery wire tip exits through the longitudinal slot in the microcatheter, which radially aligns the mesh cover to the aneurysm entrance, and guiding the distal tip of the delivery wire into the aneurysm. The method also includes withdrawing the microcatheter in a proximal direction while maintaining a position of the delivery wire so that the self-expanding frame of the vascular flow diverter opens against an inner wall of the blood vessel and the distal tip of the delivery wire guides the mesh cover of the vascular flow diverter across the neck of the aneurysm.

In another example, the method also includes confirming, via a radiological imaging device, that the distal tip of the delivery wire is located inside the aneurysm. In another example, the method includes withdrawing the delivery wire into the microcatheter and withdrawing the delivery wire and the microcatheter from a patient.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is a drawing of a flow diverter illustrating its primary components and their relationship to each other, in accordance with the present disclosure.

FIG. 2 is a drawing of a microcatheter for delivering the flow diverter, illustrating its primary components and their relationship to each other, in accordance with the present disclosure.

DETAILED DESCRIPTION

Figure 3:
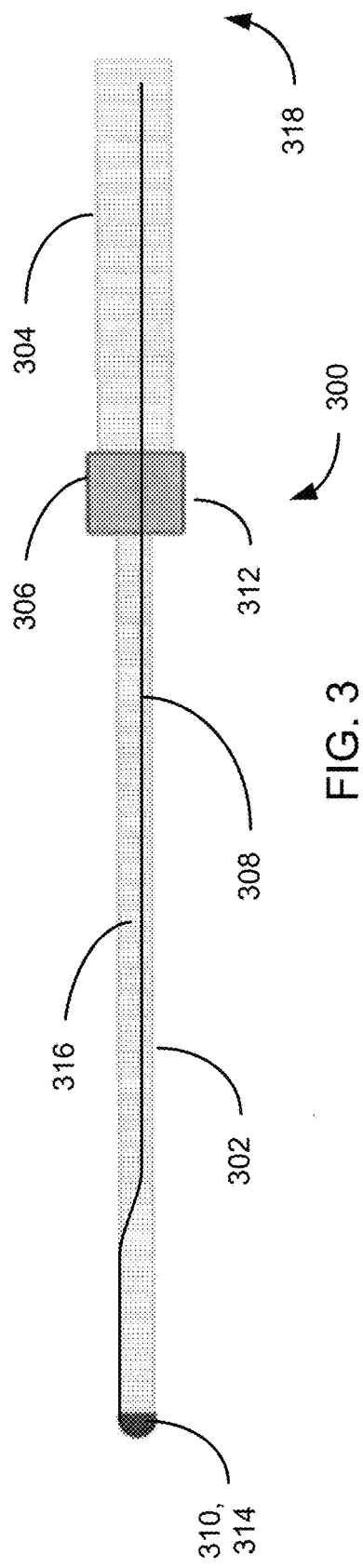
FIG. 3 is a drawing of one example of a delivery wire for delivering the flow diverter, illustrating its primary components and their relationship to each other, in accordance with the present disclosure.

Referring now to the Figures, in which like reference numerals represent like parts, various examples of the computing devices and methods will be disclosed in detail.

FIG. 1 is a drawing of a flow diverter 100. The flow diverter 100 includes a self-expanding tubular mesh frame 102, which has high porosity. "High porosity" indicates that the mesh of the component includes more open space than vessel coverage. A high porosity component thus has a low metal-to-artery ratio. The metal-to-artery ratio is calculated by dividing the cylindrical area that the device covers in the artery by the total cylindrical area of the artery segment containing the device. The tubular mesh frame 102 has an expanded (free) state and a collapsed state. The expanded state is shown. The tubular mesh frame 102 must be externally compressed to enter the collapsed state and resumes the expanded state under the proper conditions. In some examples, the tubular mesh frame 102 can automatically resume the expanded state by action of internal tension forces as soon as an external constraint is removed. In other examples, the tubular mesh frame 102 may resume the expanded state in response to a thermal input or an electrical signal. On example of such a tubular mesh frame 102 can be fabricated from shape-memory alloy such as nickel-titanium alloy (nitinol).

A low porosity (high metal-to-artery ratio) mesh cover 104 is incorporated with the tubular mesh frame 102. The mesh cover 104 is placed over the mid-section of the tubular mesh frame 102. The mesh cover 104 generally may have a circular, rounded, or oblong shape 110. An opening 106 is formed in the center of the mesh cover 104. The opening 106 is sufficiently large to allow a guiding device, such as a steerable radiopaque guidewire (or microcatheter) to pass through it.

In some examples, the mesh cover 104 may be integrated as part of the tubular mesh frame 102. In one example, the mesh cover 104 may be woven from the same filaments as the tubular mesh frame 102, but in a tighter pattern. In other examples, the mesh cover 104 may be a separate element attached to the tubular mesh frame 102. In one such example the mesh cover 104 may attached to the tubular mesh frame 102 by welding. In another such example the mesh cover 104 may attached to the tubular mesh frame 102 by an adhesive. In another example, filaments of the mesh cover 104 may be interlaced with the filaments of the tubular mesh frame 102. In another such example the mesh cover 104 may attached to the tubular mesh frame 102 by temporarily and locally melting either the mesh cover 104 or tubular mesh frame to fuse the two together (as opposed to welding, which would temporarily melt both to create the bond). In another such example the mesh cover 104 may be attached to the tubular mesh frame 102 by sandwiching the mesh cover 104 between layers of the tubular mesh frame 102, or vice versa.

Figure 7:
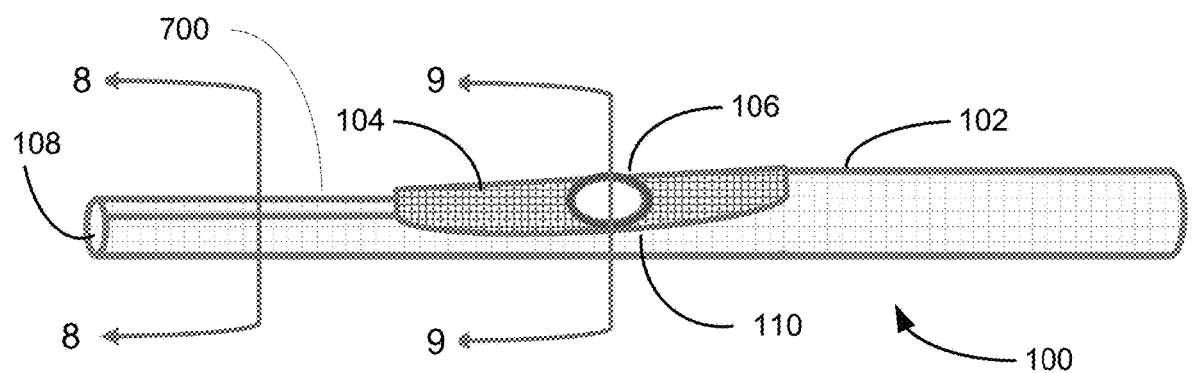
FIG. 7 is a drawing of a flow diverter in the collapsed configuration, in accordance with the present disclosure
Figure 8:
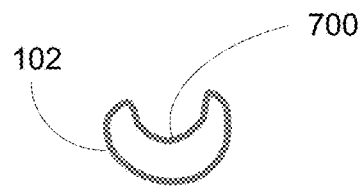
FIG. 8 is a drawing of a cross-section of the collapsed flow diverter of FIG. 7, in accordance with the present disclosure
Figure 9:
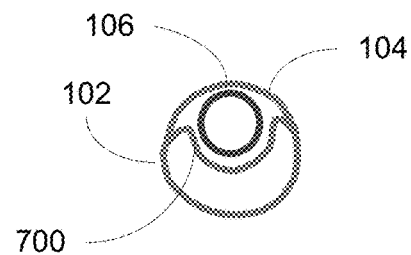
FIG. 9 is a drawing of another cross-section of the collapsed flow diverter of FIG. 7, in accordance with the present disclosure

FIG. 7 illustrates the flow diverter 100 in the collapsed state. A collapsed portion 700 is formed in the tubular mesh frame 102 and the mesh cover 104 to accommodate a distal section 302 of a delivery wire 300 while the flow diverter is advanced through a microcatheter 200 for placement over an aneurysm (see below for more detail on tools and techniques for delivering and placing the flow diverter 100). FIG. 8 illustrates a cross-section of the collapsed flow diverter 100 through the tubular mesh frame 102 only. The collapsed flow diverter 100 can be seen more clearly in this cross-sectional view. FIG. 9 illustrates a cross-section of the collapsed flow diverter 100 through the center of the opening 106. As such, the relationship between the collapsed portion 700, the opening 106, the tubular mesh frame 102, and the mesh cover 104 can be seen.

FIG. 2 illustrates a microcatheter 200 for delivering the flow diverter 100. The microcatheter 200 has a tubular outer wall 202, a distal end 204, a proximal end 206, and a longitudinal axis 210 which is approximately coincident with the center of the tubular outer wall 202 along its length. The distal end includes a transverse opening 208 and a longitudinal opening 212. In some examples, the transverse opening 208 may be substantially perpendicular to the longitudinal axis 210. In some examples, the transverse opening 208 may be at an angle to the longitudinal axis 210.

The longitudinal opening 212 may be a slot or similar shape having a long dimension following the length of the microcatheter 200 and a short dimension on the circumference (or other non-circular perimeter) of the microcatheter 200. One end of the longitudinal opening 212 intersects 214 the transverse opening 208 at the distal end 204 of the microcatheter 200. The other end of the longitudinal opening may be square (i.e. having right-angle corners with or without radii), semicircular, or elliptical.

The distal end 24 of the microcatheter 200 may also include a radiopaque marker 218. The radiopaque marker 218 allows a clinician to observe the location of the distal end 204 of the microcatheter 200 within a patient's vascular system using a radiological instrument. For example, a clinician may use fluoroscopy, digital subtraction angiography, rotational angiography, computed tomography (CT), cone beam CT, or the like to observe the location of the radiopaque marker 218. In some examples, the radiopaque marker 218 may be a circular band or ring shape. In some further examples, the circular band may be a split ring shape, where the split in the ring is aligned with the longitudinal opening 212.

FIG. 3 illustrates a steerable delivery wire 300 for delivering the flow diverter 100. The delivery wire 300 is deployed within the microcatheter 200. The delivery wire 300 includes a distal section 302, a proximal section 304, and a junction 306 between the distal section 302 and/or the proximal section 304. At least a portion of the distal section 302 of the delivery wire 300 is configured to adopt a curved configuration. The distal section 302 has a smaller cross section than the proximal section 304. In some examples, the distal section 302 can slide relative to the proximal section 304. This allows the tip of delivery wire to be retracted after the flow diverter is placed across the neck of the aneurysm. In some examples, both the distal section 302 and the proximal section 304 have circular cross sections. In other examples, the distal section 302 and the proximal section 304 may have non-circular cross-sections. For instance either of the distal section 302 or the proximal section 304 may have elliptical, oblong, oval, triangular, or quadrilateral cross sections. In addition, in some examples the non-circular cross section of either the distal section 302 or the proximal section 304 may not have a consistent angular orientation along the length of the delivery wire 300. The distal section 302 includes a tip 310. In some examples, the tip 310 may include a radiopaque marker 314.

In one example, the portion of the distal section 302 of the delivery wire 300 configured to adopt a curved configuration is preset into the curved configuration and reverts to the curved configuration from a straightened configuration when deployed from the microcatheter. Thus, the section is in the curved configuration when the delivery wire is in its free state. When the delivery wire is inserted into the microcatheter the inner diameter of the microcatheter constrains the delivery wire and forces the curved portion into a straightened configuration. When the delivery wire is deployed from the microcatheter the section reverts to its preset curved configuration. The curved section may be formed from flexible resilient materials. For example, the curved section may be formed from spring steel or may be heat-treated to form the curved section in its free state.

In another example, at least one pull wire 308 is positioned within the lumen 316 of the delivery wire 300. The pull wire 308 or wires are attached to the tip 310 of the distal section 302 so that when a pull wire 308 is pulled from a proximal end 318 of the proximal section 304 of the delivery wire 300, it causes at least a portion of the distal section 302 near the tip 310 to curve. This allows a clinician to guide the tip 310 of the distal section 302 of the delivery wire 300 into an aneurysm. In some examples, the entire distal section 302 may curve when the pull wire 308 is pulled. In other examples, a portion of the proximal section 304 may also curve when the pull wire 308 is pulled.

The junction 306 between the distal section 302 and the proximal section 304 has a cross section at least as large as the proximal section 304. The junction 306 is used to push the flow diverter 100 out of the microcatheter 200 for placement across the neck of an aneurysm, as will be explained in greater detail below. In some examples, the junction 306 may also include a radiopaque marker 312.

Figure 4:
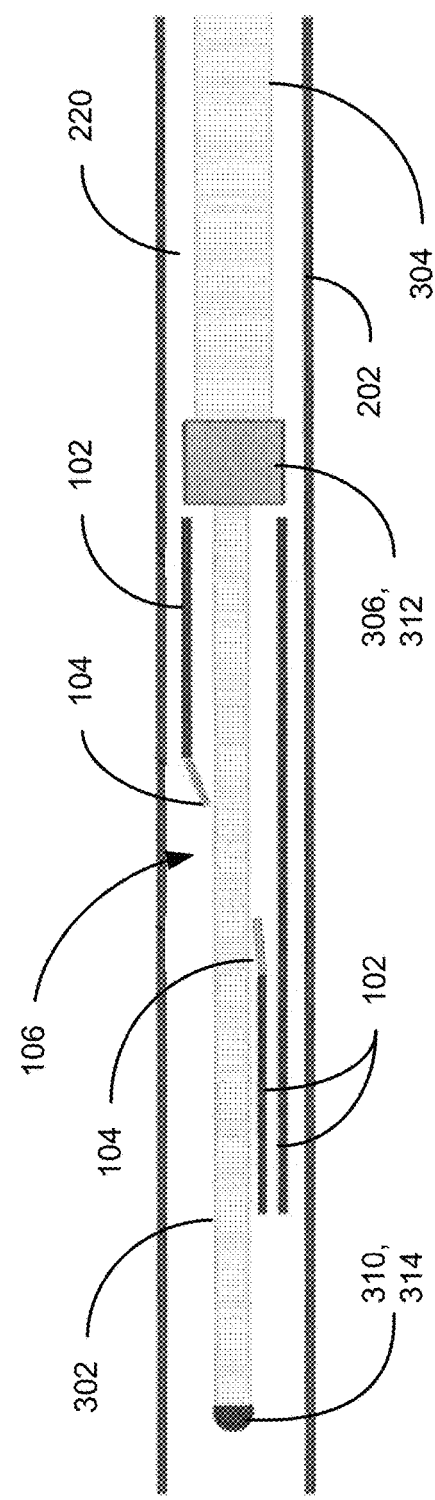
FIG. 4 is a cross-sectional view of one example of the microcatheter with the delivery wire and flow diverter installed in preparation for placement in a blood vessel, in accordance with the present disclosure.

FIG. 4 is a cross-sectional view illustrating the microcatheter 200 with the delivery wire 300 and flow diverter 100 installed in preparation for placement in a blood vessel. The flow diverter 100 is mounted over distal section 302 of the delivery wire 300 by guiding the opening 106 over the distal section 302 until the tubular mesh frame 102 meets the junction 306 between the distal section 302 and the proximal section 304 of the delivery wire 300. The tubular mesh frame 102 of the flow diverter 100 is then compressed into its collapsed state, pre-loaded into an introducer (not shown), and transferred into the microcatheter lumen 220.

FIGS. 5a-5f are a series of drawings illustrating one example of a sequence of steps for placing the flow diverter 100 in a blood vessel 514 to occlude an aneurysm 512. At FIG. 5a the microcatheter 200 is advanced across the neck 516 of the aneurysm 512. At FIG. 5b, the radial alignment of the longitudinal opening 212 of the microcatheter 200 with the aneurysm is checked and adjusted, if necessary. The tip 310 of the distal section 302 of the delivery wire 300 is then advanced out of the microcatheter 200 and guided through the neck 516 of the aneurysm 512. The delivery wire may have a preset curvature, as described above, or may be guided using a pull wire 308. The delivery wire is engaged with the implant by passing through opening 106, but is not attached. At FIG. 5c, after confirming that the tip 310 of the distal section 302 is seated in the aneurysm 512, the flow diverter 100 may be deployed. The flow diverter 100 is deployed by pulling back on the microcatheter 200 while maintaining the position of the delivery wire 300.

Figure 5A:
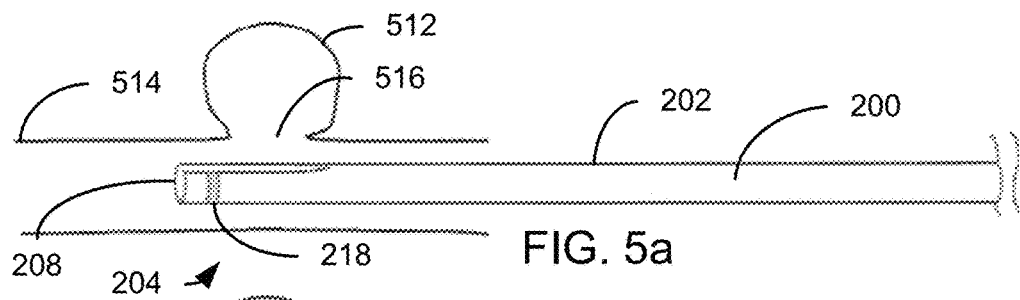
FIGS. 5a-5f are a series of drawings of an aneurysm in a blood vessel, illustrating an example of a sequence of steps for placing the flow diverter in a blood vessel to occlude an aneurysm, in accordance with the present disclosure.
Figure 5B:
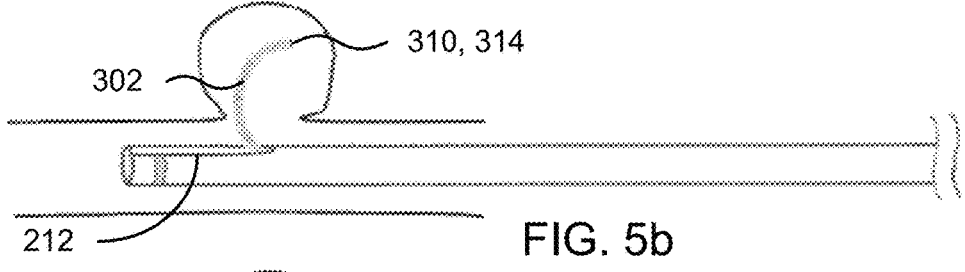
Figure 5C:
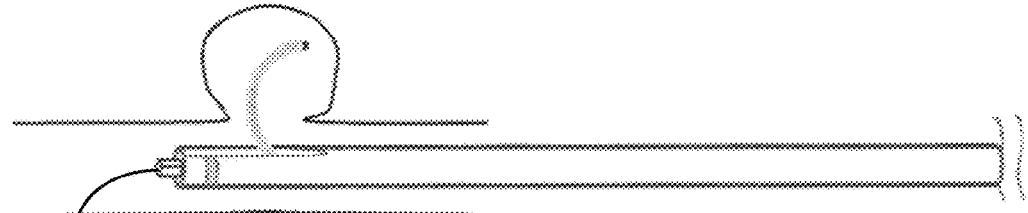
Figure 5D:
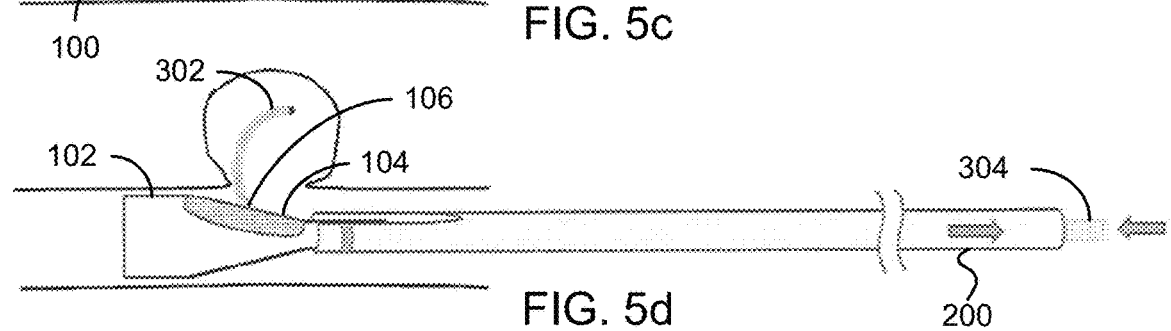
Figure 5E:
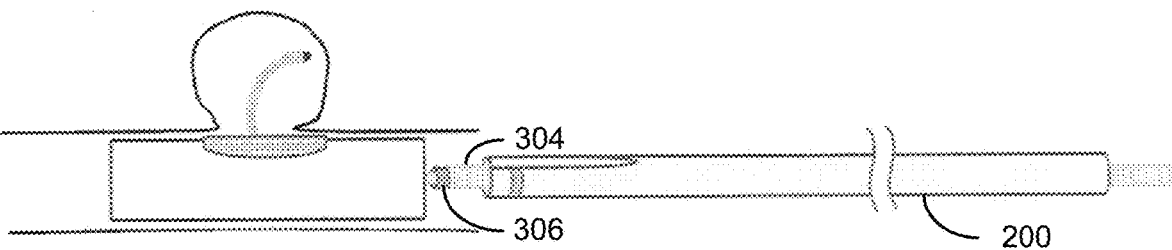
Figure 5F:
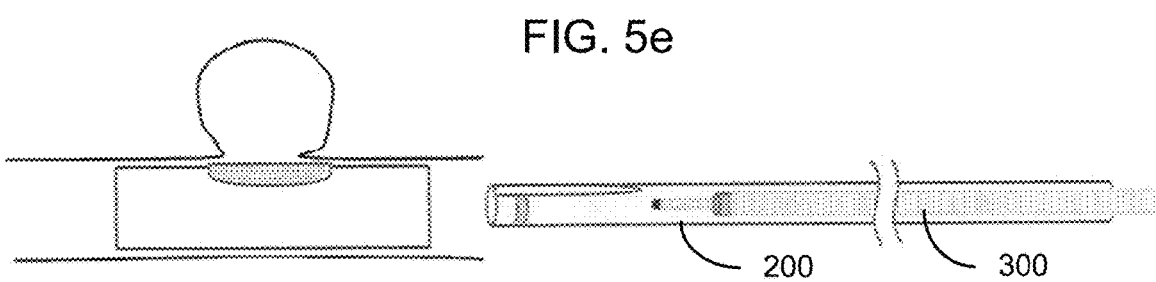

At FIG. 5d, the self-expanding tubular frame 102 opens against the interior of the blood vessel 514 while the flow diverter 100 is guided along the distal section 302 of the delivery wire 300 by its opening 106. At FIG. 5e, the flow diverter 100 is fully deployed from the microcatheter 200 and expanded. At FIG. 5f, the delivery wire 300 is withdrawn back into the microcatheter 200 and they can both be withdrawn from the patient.

Figure 6:
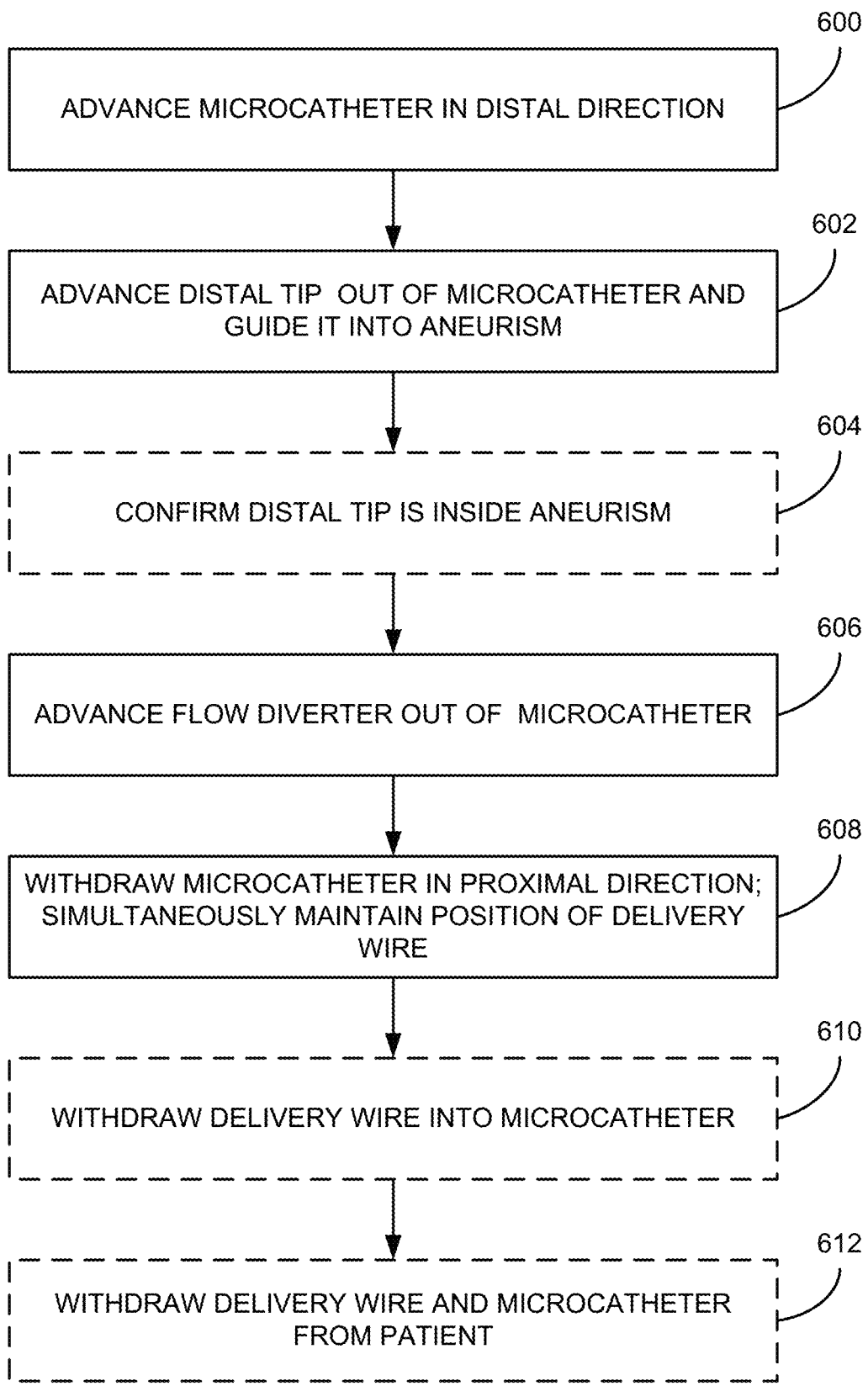
FIG. 6 is a flow chart illustrating an example of a sequence of steps for placing the flow diverter in a blood vessel to occlude an aneurysm.

FIG. 6 is a flow chart illustrating the sequence of steps for placing the flow diverter in a blood vessel to occlude an aneurysm. At 600, the clinician advances the microcatheter in the distal direction across a neck of an aneurysm in a blood vessel. At 602, the clinician advances the distal tip of the delivery wire out of the microcatheter and guides the distal tip of the delivery wire into the aneurysm. At 604, the clinician confirms, via a radiological imaging device, that the distal tip of the delivery wire is located inside the aneurysm. The radiological imaging device may include, for example, fluoroscopy, digital subtraction angiography, rotational angiography, computed tomography (CT), cone beam CT, or the like. At 606, the clinician deploys the flow diverter from the microcatheter. At 608, the clinician withdraws the microcatheter in the proximal direction while maintaining the position of the delivery wire so that the self-expanding frame of the vascular flow diverter opens against the inner wall of the blood vessel while the distal tip of the delivery wire guides a mesh cover of the vascular flow diverter across the neck of the aneurysm. At 610, the clinician withdraws the delivery wire into the microcatheter. At 612, the clinician withdraws the delivery wire and the microcatheter from the patient.

To facilitate an understanding of the principals and features of the disclosed technology, illustrative examples are explained above. The components described as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

It must also be noted that, as used in the specification and the appended claims, the singular forms "a," "an" and "the" include plural referents unless the context clearly dictates otherwise.

By "comprising" or "containing" or "including" is meant that at least the named component, element, or method step is present in the article or method, but does not exclude the presence of other component, materials, elements, method steps, even if the other such component, materials, elements, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain examples of the technology and also to enable any person skilled in the art to practice certain examples of this technology, including making and using any apparatuses or systems and performing any incorporated methods. The patentable scope of certain examples of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A vascular flow diverter system comprising:
   vascular flow diverter including a tubular mesh framework configured to transition from a collapsed configuration to an expanded configuration in response to the vascular flow diverter being deployed, the tubular mesh framework having a first porosity; and
   a mesh cover surrounded by the tubular mesh framework, the mesh cover comprising:
      an outer perimeter; and
      an opening formed in a center of the mesh cover and located within the outer perimeter, the opening sized to allow a guide member to extend through the opening, the mesh cover, and the tubular mesh framework,
   wherein the mesh cover extends at least partially around a circumference of the tubular mesh framework,
   wherein the mesh cover is configured to conform to a shape of the tubular mesh framework, the mesh cover having a second porosity, the first porosity being greater than the second porosity, and
   the system further comprising a delivery device comprising a lumen receiving the vascular flow diverter, the delivery device comprising:
   a microcatheter comprising a tubular outer wall, a distal end, and a proximal end, the distal end comprising a transverse opening and a longitudinal opening, where the transverse opening is perpendicular entirely along a cross-section of the distal end to a longitudinal axis of the microcatheter and the longitudinal opening is substantially parallel to the longitudinal axis of the microcatheter, and the longitudinal opening intersects the transverse opening;
   a guide member comprising a distal section, a proximal section, and a junction between the distal section and the proximal section, where:
      the distal section has a smaller cross section than the proximal section;
      the distal section is steerable from a proximal end of the proximal section, where at least a portion of the distal section of the guide member is configured adopt a curved configuration; and
      the junction is configured to push the vascular flow diverter; and
      a pull wire is positioned in a lumen of the guide member and terminates at a tip of the distal section,
   wherein a proximal end of the pull wire may be pulled to form the curved configuration in at least a portion of the distal section, and
   wherein the distal section of the guide member is sufficiently contiguous to contain, when the pull wire is pulled to form the curved configuration in the distal section, an entire length of a portion of the pull wire extending from the tip of the distal section, through the distal section, and to the junction.

2. The vascular flow diverter system of claim 1, wherein the outer perimeter of the mesh cover is rounded.

3. The vascular flow diverter system of claim 1, wherein the outer perimeter of the mesh cover is circular.

4. The vascular flow diverter system of claim 1, wherein the mesh cover is integrated with the tubular mesh framework.

5. The vascular flow diverter system of claim 1, wherein the mesh cover is separate from and attached to the tubular mesh framework.

6. The vascular flow diverter system of claim 1, wherein the mesh cover is attached to the tubular mesh framework by welding.

7. The vascular flow diverter system of claim 1, wherein the mesh cover is attached to the tubular mesh framework by interlacing mesh strands of the mesh cover with mesh strands of the tubular mesh framework.

8. The vascular flow diverter system of claim 1, wherein the tubular mesh framework transitions from the collapsed configuration to the expanded configuration in response to an electrical signal.

9. The vascular flow diverter system of claim 1, wherein the mesh cover is attached to the tubular mesh framework by positioning the mesh cover between a first layer of mesh strands of the tubular mesh framework and a second layer of mesh strands of the tubular mesh framework.

10. A vascular flow diverter system comprising:
   a vascular flow diverter including a stent configured to transition from a collapsed configuration to an expanded configuration in response to the vascular flow diverter being deployed, the stent having a first porosity; and a mesh cover surrounded by the stent, the mesh cover comprising:
an outer perimeter; and
an opening formed in a center of the mesh cover and located within the outer perimeter, the opening sized to allow a guide member to extend through the opening, the mesh cover, and the stent, wherein the mesh cover extends at least partially around a circumference of the stent, wherein the mesh cover is configured to conform to a shape of the stent, the mesh cover having a second porosity, the first porosity being greater than the second porosity, and the system further comprising a delivery device comprising a lumen receiving the vascular flow diverter, the delivery device comprising:

a microcatheter comprising a tubular outer wall, a distal end, and a proximal end, the distal end comprising a transverse opening and a longitudinal opening, where the transverse opening is perpendicular entirely along a cross-section of the distal end to a longitudinal axis of the microcatheter and the longitudinal opening is substantially parallel to the longitudinal axis of the microcatheter, and the longitudinal opening intersects the transverse opening;

a guide member comprising a distal section, a proximal section, and a junction between the distal section and the proximal section, wherein:
the distal section has a smaller cross section than the proximal section;
the distal section is steerable from a proximal end of the proximal section, where at least a portion of the distal section of the guide member is configured to adopt a curved configuration; and
the junction is configured to push the vascular flow diverter; and a pull wire is positioned in a lumen of the guide member and terminates at a tip of the distal section,
wherein a proximal end of the pull wire may be pulled to form the curved configuration in at least a portion of the distal section, and
wherein the distal section of the guide member is sufficiently contiguous to contain, when the pull wire is pulled to form the curved configuration in the distal section, an entire length of a portion of the pull wire extending from the tip of the distal section, through the distal section, and to the junction.

11. The vascular flow diverter system of claim 10, wherein the outer perimeter of the mesh cover is rounded.

12. The vascular flow diverter system of claim 10, wherein the outer perimeter of the mesh cover is circular.

13. The vascular flow diverter system of claim 10, wherein the mesh cover is integrated with the stent.

14. The vascular flow diverter system of claim 10, wherein the mesh cover is separate from and attached to the stent.

15. The vascular flow diverter system of claim 10, wherein the mesh cover is attached to the stent by welding.

16. The vascular flow diverter system of claim 10, wherein the mesh cover is attached to the stent by interlacing mesh strands of the mesh cover with mesh strands of the stent.

17. The vascular flow diverter system of claim 10, wherein the stent transitions from the collapsed configuration to the expanded configuration in response to an electrical signal.

18. The vascular flow diverter system of claim 10, wherein the mesh cover is attached to the stent by positioning the mesh cover between a first layer of mesh strands of the stent and a second layer of mesh strands of the stent.

\* \* \* \* \*